United States Patent [19]

Isaacs

[11] Patent Number: 4,590,172

[45] Date of Patent: May 20, 1986

[54] PREPARATION OF SOLUBLE MOLYBDENUM CATALYSTS FOR EPOXIDATION OF OLEFINS

[75] Inventor: Bruce H. Isaacs, Newtown Square, Pa.

[73] Assignee: Atlantic Richfield Company, Los Angeles, Calif.

[21] Appl. No.: 665,422

[22] Filed: Oct. 26, 1984

[51] Int. Cl.[4] .............................................. B01J 23/28
[52] U.S. Cl. .................................. 502/160; 502/170; 549/529
[58] Field of Search ................................ 502/160, 170

[56] References Cited

U.S. PATENT DOCUMENTS

| | | | |
|---|---|---|---|
| 3,362,972 | 1/1968 | Kollar | 260/414 |
| 3,434,975 | 3/1969 | Sheng et al. | 502/160 |
| 3,453,218 | 7/1969 | Sheng et al. | 502/160 |
| 3,595,891 | 7/1971 | Cavitt | 502/170 X |
| 3,819,663 | 6/1974 | Levine et al. | 260/348.5 L |

FOREIGN PATENT DOCUMENTS

| | | |
|---|---|---|
| 1060122 | 2/1967 | United Kingdom . |
| 422437 | 10/1974 | U.S.S.R. |

*Primary Examiner*—Patrick P. Garvin
*Attorney, Agent, or Firm*—Michael S. Jarosz

[57] ABSTRACT

Production of molybdenum-containing stable catalyst solutions especially adapted for use in the epoxidation of olefinic compounds with an organic hydroperoxide by reaction of molybdenum metal with a peroxy compound and an organic dicarboxylic acid in the presence of monohydroxy alcohol is provided.

19 Claims, No Drawings

PREPARATION OF SOLUBLE MOLYBDENUM CATALYSTS FOR EPOXIDATION OF OLEFINS

BACKGROUND OF THE INVENTION

The production of oxirane compounds such as propylene oxide and its higher homologs is described in Kollar U.S. Pat. No. 3,351,635. In accordance with the Kollar process, the oxirane compound may be prepared by epoxidation of an olefinically unsaturated compound (for example, propylene) by use of organic hydroperoxide and a suitable metal catalyst, such as a molybdenum compound. Kollar teaches that activity of the metal catalyst disclosed therein for expoxidation of primary olefins is high and can lead to high selectivity of propylene to propylene oxide. These selectivities are obtained at high conversions of hydroperoxide (50% or higher) which conversion levels are important for commercial utilization of this technology. In accordance with the Kollar process, the epoxidation reaction proceeds under pressure in a liquid state, and accordingly, a liquid solution of the metal catalyst is desired.

In the preparation of metal compounds, for example, molybdenum salts, for the aforementioned purposes, various techniques have been used, many of which have been found to be extremely difficult to carry out efficiently on a commercial scale, and hence expensive, particularly for preparing hydrocarbon soluble compositions containing a high molybdenum content. Kollar U.S. Pat. No. 3,362,972 is concerned with preparation of molybdenum salts of carboxylic acids wherein molybdenum trioxide is reacted with oxalic acid in the presence of hexanoic acid. Sheng et al. U.S. Pat. No. 3,434,975 reports the preparation of molybdenum containing catalysts by reaction of molybdenum metal with peroxy compounds in the presence of a saturated alcohol. Sheng et al. U.S. Pat. No. 3,453,218 discloses the preparation of molybdenum containing epoxidation catalysts by reaction of molybdenum metal with a combination of tertiary butyl hydrogen peroxide and formic acid at low temperature. Ziolkowski et al. Polish Pat. No. 100,561 discloses the preparation of molybdenum-containing catalysts by treating $Mo(OH)_5$ with certain aliphatic or dicarboxylic acids and with an alpha-hydroxy acid or with certain diols or beta-diketones in an organic solvent. Ziolkowlski et al. Polish Pat. No. 103,742 is concerned with preparation of complexes of molybdenum from $Mo(O)(OH)_3$ and oxalic acid, lactic acid and ethylene glycol deposited on certain carriers. Sobczak et al., *Journal Less-Common Met.*, Vol. 54, pp. 149-52 (1977) describe the reaction of molybdenum complexes with dicarboxylic acids, such as oxalic acid. Finally, Kuzimina et al., *Izv. Timiryazev. Sel'skokhoz Akad.* (2), 224-8 (1970) describe complex forming reactions of molybdenyl ions with certain organic dicarboxylic acids, including oxalic acid.

However, each of these prior art processes are deficient by requiring expensive starting materials or forming carboxylates or complex molybdenum compositions which contain relatively low metal content and/or in requiring a number of steps in order to produce the desired high molybdenum-containing soluble catalyst composition.

Accordingly, it is an object of the present invention to provide a simple, inexpensive method for the production of molybdenum-containing catalysts having a high metal content which are suitable for use in the epoxidation of olefins with organic hydroperoxides to produce the corresponding oxirane compounds.

A further object of the present invention is to provide molybdenum-containing catalyst compositions which result in increased selectivity to desired alkylene oxide, e.g. propylene oxide, product in the epoxidation of a primary olefin, e.g. propylene while at the same time reducing production of undesired by-products.

An additional object of the present invention is to provide a process for the preparation of molybdenum-containing epoxidation catalysts from molybdenum metal, which process is characterized by improved dissolution rates of the molybdenum metal, thereby reducing hydroperoxide consumption, lowering molybdenum losses and providing catalyst preparation at increased productivity.

SUMMARY OF THE INVENTION

It has now been discovered that stable solutions of molybdenum-containing catalyst compositions, useful as organic soluble epoxidation catalysts and containing increased quantities of molybdenum is the catalyst composition than heretofore obtainable, may be prepared by reacting molybdenum metal with a peroxy compound, such as an organic hydroperoxide, organic peracid, or hydrogen peroxide, or admixtures thereof, and a certain organic dicarboxylic acid in the presence of a monohydroxy alcohol and optionally, in the presence of an additional secondary solvent, such as a polyhydroxy alcohol. This discovery is deemed surprising since it is known in the art, for example from British Pat. No. 1,060,122 and from Levine et al U.S. Pat. No. 3,819,663, that it is desirable to exclude acids from such epoxidation systems since acid impurities, such as carboxylic acids, destablize molybdenum-containing catalyst solutions or interefere with the epoxidation reaction in which the molybdenum-containing catalyst composition is employed. This improved result is achieved without being accompanied by deleterious corrosion, normally accompanied by the presence of acidic components in chemical process applications. In addition, it has also been found that the high molybdenum containing catalyst composition solutions of the invention, provide higher yields in epoxidation of olefins with organic hydroperoxides to the desired alkylene oxide compounds, under the same process conditions, than catalyst compositions prepared in the absence of organic dicarboxylic acid; this discovery is further surprising, since it is known that the presence of acids decreases the yield to desired alkylene oxide product.

The molybdenum-containing catalyst compositions of the invention may be employed in the aforestated expoxidation reaction as fresh stable catalyst solutions, or admixed with the evaporation residue obtained from the previous epoxidation of an olefinic compound with an organic hydroperoxide in the presence of a molybdenum epoxidation catalyst, to a wiped film evaporation at elevated temperatures in accordance with the method described and claimed in the above-identified Levine et al U.S. Pat. No. 3,819,663, the disclosure of which is hereby incorporated by reference.

As used in the present specification and the annexed claims, the term "stable catalyst solution" is intended to mean a molybdenum-containing solution which will not precipitate an appreciable amount, less than about 1% of the molybdenum contained in the solution, of molybdenum, upon heating to a temperature of about 85° C. over about a period of at least four hours, followed by standing at a temperature of 50° C. for a period of at least ten hours.

Accordingly, the present invention permits preparation of a molybdenum-containing catalyst compositions which contain higher proportions of molybdenum than previously have been capable of preparation for use in organic soluble epoxidation reactions from a readily available and comparatively inexpensive source, molybdenum metal, while at the same time, reducing or totally eliminating the need for expensive reaction media, such as organic polyhydroxy alcohols for dissolution of the molybdenum metal. In addition, use of the molybdenum-containing composition provides improved selectivity and yields of desired alkylene oxide products. These and other objects of the invention will become apparent from the following descriptions and examples.

DETAILED DESCRIPTION OF THE INVENTION

The molybdenum-containing catalyst composition of the invention is prepared by direct reaction of metallic molybdenum with a peroxy compound and a certain organic dicarboxylic acid in the presence of a monohydroxy alcohol, or optionally an admixture of a monohydroxy alcohol with a polyhydroxy alcohol, present as a diluent in the formulation of the desired molybdenum-containing catalyst composition.

The metallic molybdenum contemplated may be present in any physical form, such as sheet, foil, lumps, rods or powder. In the commercial production of the molybdenum-containing catalyst compositions of the invention, the molybdenum metal is employed in the form of a powder, preferably since the higher surface area per unit weight of molybdenum promotes faster reaction. Such powders, in general, exhibit a surface area of at least 0.05 square meters per gram, and preferably, of at least 0.2 square meters per gram.

The organic hydroperoxides which are employable in the present invention are characterized by being liquid at the reaction conditions employed and by having the structure ROOH, wherein R may be alkyl, alkenyl, aryl, alkaryl, aralkyl, cycloalkyl, cycloalkenyl and similar radicals which also contain functional groups. Examples of such hydroperoxide employable in the preparation of the molybdenum-containing catalyst of the invention include tertiary butyl hydroperoxide, tertiary amyl hydroperoxide, cumene hydroperoxide, tetralin hydroperoxide, alphahydroperoxy diisopropylketone, the hydroperoxide of 2-methylbutene-2, the hydroperoxide of octene-1, the hydroperoxide of 2,6-di-tertiary butyl paracresol, and the like. Tertiary butyl hydroperoxide is preferred since, upon reduction, it is converted into the corresponding alcohol which is a convenient solvent for the epoxidation reaction, when propylene, for example, is employed as the starting olefin. When the peroxy compound is employed as an organic hydroperoxide, such hydroperoxide is preferably present in the form of a 30 to 40 percent, by weight, solution thereof. Included among the various peracids which may be utilized are performic acid, peracetic acid, trifluoroperacetic acid, perbenzoic acid and the like; of these, peracetic acid is particularly preferred.

The organic dicarboxylic acids employable in preparation of the molybdenum-containing catalyst compositions of the invention include aliphatic, cycloaliphatic and aromatic dicarboxylic acids of from 2 to 18 carbon atoms, preferably, 2 to 8 carbon atoms in the case of aliphatic and cycloaliphatic dicarboxylic acids, and 8 to 12 carbon atoms in the case of aromatic dicarboxylic acids. Organic dicarboxylic acids of such character which contain the carboxylic acid groups on adjacent carbon atoms are particularly preferred. Illustrative examples of suitable organic dicarboxylic acids employable herein include oxalic acid, malonic acid, succinic acid, glutaric acid, adipic acid, maleic acid, fumaric acid, phthalic acid, isophthalic acid, terephthalic acid, and 1,2-naphthalene dicarboxylic acid. Oxalic and phthalic acid constitute particularly preferred species of employable organic dicarboxylic acids in preparation of the catalyst compositions of the present invention.

Suitable monohydroxy alcohols employable in formulation of the liquid catalyst composition of the invention include aliphatic alcohols of 1 to 12 carbon atoms, preferably 4 to 10 carbon atoms. Although the monohydroxy compound employable herein may be substituted with functional groups which are inert to the reactants present, for example, halo-, such as chloro or fluoro; nitro; cyano; carbonyl; and carboxyl, the readily available aliphatic monohydroxy-containing organic compounds containing only carbon, hydrogen and oxygen are particularly satisfactory for use in the present invention. Illustrative suitable monohydroxy compounds include methanol, ethanol, propanol, n-hexanol, 2-ethylhexanol and particularly preferred is tertiary butyl alcohol. The monohydroxy alcohol portion of the admixture is generally adjusted so that sufficient monohydroxy alcohol is introduced to provide the maximum concentration of molybdenum in the form of a stable solution in accordance with the invention. In general, the monohydroxy alcohol is employed in amount at least about 25 and, preferably between about 50 and 200, parts per part of molybdenum, to be solubilized.

The polyhydroxy compound suitable for use in formulation of the aforementioned molybdenum-catalyst compositions, if employed, also generally contain up to about 12 carbon atoms. Such polyhydroxy compounds normally contain 2 to 4 hydroxyl groups, but preferably contain 2 hydroxyl groups, i.e., monoalkylene glycols or derivatives thereof, such as glycol ethers, provided these compounds contain at least one hydroxyl group. As is the case in connection with the monohydroxy alcohol referred to above, the polyhydroxy compounds may be substituted with functional groups which are inert to the reactants present. Polyhydroxy compounds containing solely carbon, hydrogen and oxygen are particularly preferred. Typical illustrative polyhydroxy compounds employable in preparation of the catalyst compositions of the invention include ethylene glycol, propylene glycol, butylene glycols such as 1,4-butanediol, catechol and alkylene ethers of such glycols, including the methyl and ethyl ethers thereof. In general, when the diluent comprises an admixture of monohydroxy and polyhydroxy alcohols, the polyhydroxy alcohol is employed in an amount of up to about 20 percent, preferably up to about 10%, by volume, of the monohydroxy alcohol employed. However, large excesses of polyhydroxy alcohol should be avoided since such compounds have a deleterious effect on subsequent epoxidation reactions, and hence, large excesses are not favored for molybdenum solubilization.

The quantities of reactants employed in formulation of the molybdenum-containing compositions of the invention may be varied over wide ranges. In general, the weight ratio of molybdenum metal to peroxy compound, illustratively, an organic hydroperoxide, such as tertiary butyl hydroperoxide, may range from about 1:2 to 1:20, with ranges of 1:15 to 1:10 being preferred. The weight ratio of molybdenum metal to monohydroxy alcohol also may vary over wide limits, the preferred range being, however, from about 1:50 to 1:200. When an admixture of monohydroxy and polyhydroxy alcohols is employed, the ratio of molybdenum to monohydroxy alcohol may be as low as 1:4 to 1:100, with from about 75 to 99 weight percent of the total alcohol present being a monohydroxy alcohol. In general, the peroxy compound is present in an amount of at least about 1:2 and preferably between about 1:5 and 1:10 moles per mole of molybdenum to be solubilized.

In general, the organic dicarboxylic acid is employed in amount ranging from about 0.2 to 4 moles, preferably 0.5 to 2.0 moles per mole of molybdenum charged. The final molybdenum-containing catalyst composition of the invention is characterized by containing of from about 0.1 to about 3 percent of molybdenum by weight, preferably from about 0.5 to about 2 percent, molybdenum, by weight.

The temperature employed to solubilize the molybdenum metal in formulation of the catalyst of the molybdenum-catalyst compositions in the invention may range between about 25° C. and about 120° C., and preferably between about 50° C. and about 100° C. Temperatures lower than about 25° C. necessitate unduly long reaction times and are not favored. A particularly convenient temperature is the reflux temperature of the liquid admixture into which the molybdenum metal is being solubilized. In general, atmospheric pressure for the solubilization reaction is suitable, although the reaction may be carried out at superatmospheric pressures when necessary to maintain the reaction mixture in the liquid phase. When the reaction is carried out at higher temperatures which would cause vaporization of the alcohol, sufficient pressure is used to maintain the liquid phase: for example, in the event methanol is employed as the monohydroxy alcohol component, use of temperatures higher than about 60° C. require that super atmospheric pressure be used to maintain the liquid state.

The time required to solubilize the molybdenum metal to a stable active solution is a function of both temperature, and nature and proportions of components of the mixture. Generally, solubilization requires a reaction time ranging from a few minutes, for example, 15 minutes at the higher temperatures, to several hours at the lower temperatures, with reaction times in the range of from about 30 minutes to 2 hours being preferred when the preferred temperature range is employed.

The molybdenum-containing catalyst composition is prepared in accordance with the process of the present invention have been found to be suitable for epoxidation of olefins, illustratively propylene, to produce the corresponding oxirane compound, propylene oxide, for example, at high yields and conversions, without production of undesirable high quantities of undesirable by-products. In general, the catalyst composition of present invention is suitable for the epoxidation of compounds having the general formula:

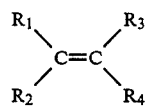

where $R_1$, $R_2$, $R_3$ and $R_4$ may be hydrogen, alkyl, aryl arylalkyl, alkaryl, alkenyl, alkadienyl or similar radicals having functional groups, in accordance with the process described and claimed in Kollar U.S. Pat. No. 3,351,635, the disclosure of which is hereby incorporated by reference. Illustrative acyclic olefinic hydrocarbons which may be epoxidized are the aliphatic normally gaseous olefins such as propylene, the butylenes and the higher olefins, including the liquid and high molecular weight solid olefins. Mono-olefinic hydrocarbons, diolefinic hydrocarbon and polyolefinic hydrocarbons may also be epoxidized by the catalyst of the present invention.

In addition to being employed as fresh catalyst solution in the above-described epoxidation reaction, the molybdenum-containing catalyst composition of the present invention finds particular use when employed together with molybdenum-containing catalyst concentrates or residues obtained from previous epoxidation processes employing a molybdenum epoxidation catalyst; in such operations, the epoxidation reaction mixture is resolved into product fractions, including a heavy liquid fraction containing the catalyst, subjecting such heavy liquid fraction to evaporation, such as a wiped film evaporation, at elevated temperatures until at least about 60% by weight of said fraction is evaporated overhead, and recycling the evaporation residue to the epoxidation reactions, as described and claimed in Levine et al U.S. Pat. No. 3,819,663, the disclosure of which is hereby incorporated by reference. When employed in such manner, the catalyst composition of the present invention is employed in quantities up to about 90 percent and preferably up to about 50 percent, by weight, of the total molybdenum containing composition required in the epoxidation reaction.

In order to illustrate practice of the invention, the following examples are provided. It is to be understood that the examples are merely illustrative and are not intended to be restrictive of the invention herein disclosed and as defined by the claims following hereto. Parts and percentages are by weight, and temperatures are in degrees Centigrade, unless otherwise specified.

EXAMPLE IA

Into a stirred glass vessel equipped with a water cooled condenser, there were charged a mixture of 0.55 parts of molybdenum metal equivalent to 11,000 ppm of molybdenum powder having a surface area of about 0.4 m²/gram, 3.6 parts of propylene glycol, 37 parts of tertiary butyl alcohol and 9 parts of a solution comprised of about 40% by weight of tertiary butyl hydroperoxide in tertiary butyl alcohol. The mixture was refluxed at atmospheric pressure (about 85°) for a period of four hours. Precipitated solids were formed. Analysis of the resultant product indicated that of the 11,000 ppm molybdenum charged, only 7600 ppm resulted in solution.

EXAMPLE IB

A mixture of 0.55 parts molybdenum metal (equivalent to 11,000 ppm molybdenum), 40 parts of tertiary butyl alcohol, 9 parts of a solution comprised of about 40% by weight of tertiary butyl hydroperoxide in tertiary butyl alcohol and 0.72 parts of oxalic acid dihydrate was refluxed four hours (about 85° C.). Analysis of the resultant solution revealed that no precipitated solids were formed and that the entire charge of 11,000 ppm molybdenum was solubilized in the reaction mixture.

EXAMPLE IC

A mixture of 0.55 parts molybdenum metal (equivalent to 11,000 ppm molybdenum), 4.4 parts of propylene glycol, 12 parts of a solution comprised of about 40% by weight of tertiary butyl hydroperoxide in tertiary butyl alcohol, 1.4 parts of oxalic acid dihydrate and 31.6 parts of tertiary butyl alcohol was refluxed for four hours at atmospheric pressure (about 85°). Analysis of the resultant solution indicated that no precipitated solids were formed and that the entire charge of 11,000 ppm molybdenum was solubilized in the reaction mixture.

In contrast, replacement of the oxalic acid dihydrate charged with tertiary butyl alcohol resulted in solubilizing only 7600 of molybdenum, of the 11,000 ppm charged, after refluxing for four hours at atmospheric pressure.

EXAMPLE IIA

A mixture of 0.55 parts of molybdenum metal, (equivalent to 11,000 ppm molybdenum) 0.72 parts of oxalic acid dihydrate, 36.7 parts of tertiary butyl alcohol and 12 parts of a solution comprised of about 40% by weight of tertiary butyl hydroperoxide in tertiary butyl alcohol was refluxed for four hours and heated overnight at 50°. Analysis of the resultant product indicated that 11,000 ppm of charged molybdenum was solubilized in the reaction mixture.

In contrast, replacement of the oxalic acid dihydrate with tertiary butyl alcohol resulted in solubilizing only 835 ppm of molybdenum, of the 11,000 ppm charged, after four hours of reflux and heating overnight (16 hours) at 50°.

EXAMPLE III

A mixture of 1 part (20,000 ppm) molybdenum metal, 8 parts of propylene glycol, 2.6 parts of oxalic acid dihydrate, 26.4 parts of tertiary butyl alcohol and 12 parts of a solution comprised of about 40 percent by weight tertiary butyl hydroperoxide in tertiary butyl alcohol was refluxed in accordance with the manner as set forth above in Example I for a period of four hours and maintained at 50° C., thereafter, for a period of 16 hours. Of the 20,000 ppm molybdenum charged, only 3400 ppm remained in solution.

In contrast, replacement of the propylene glycol with an equivalent weight of tertiary butyl alcohol resulted in a catalyst solution with 20,000 ppm of dissolved molybdenum after four hours of heating at reflux temperature and maintaining the temperature of the resultant solution for a period of 16 hours at 50°.

EXAMPLE IV

A catalyst solution was prepared by blending 3.3 parts of molybdenum metal, 144 parts of a solution comprised of about 40% by weight tertiary butyl hydroperoxide in tertiary butyl alcohol, 2.7 parts of propylene glycol and 426 parts of tertiary butyl alcohol and heating the blended mixture at reflux temperature for 2 hours. Thereafter the resultant solution was filtered to remove any undissolved solids.

A stainless steel autoclave equipped with a stirrer was charged with 60 parts of propylene, 87 parts of a solution comprised of about 40% by weight tertiary butyl hydroperoxide in tertiary butyl alcohol and 3 parts of a catalyst solution containing 5500 ppm of molybdenum obtained as described above. The epoxidation reaction was effected at 132° and about 600 psia over a period of approximately 80 minutes, which was sufficient to obtain a tertiary butyl hydroperoxide conversion of 98%, based on the tertiary butyl hydroperoxide charged. The yield of desired propylene oxide product (moles of propylene oxide produced per 100 moles of tertiary butyl hydroperoxide reacted) was 92.29%.

EXAMPLE V

A catalyst solution was prepared by blending 0.82 parts of molybdenum metal, 36 parts of a solution comprised of about 40% by weight tertiary butyl hydroperoxide in tertiary butyl alcohol, 6.7 parts of propylene glycol, 106 parts of tertiary butyl alcohol and 1.6 parts of oxalic acid dihydrate, and heating the blended mixture at reflux for a period of 2 hours. Thereafter the resultant reaction mixture was filtered to remove any remaining undissolved solids which may be present.

An epoxidation reaction as described in Example IV was carried out, except that the catalyst employed in the epoxidation reaction consisted of a catalyst solution containing 5500 ppm of molybdenum and was obtained as described above in this Example V. The yield of desired propylene oxide was 93.4%.

Example V demonstrates the obtainment of improved yields of desired propylene oxide product by use of catalyst compositions of the invention derived from oxalic acid, as compared with typical catalyst compositions disclosed in the prior art devoid of oxalic acid.

EXAMPLE VI

A stainless steel autoclave equipped with a stirrer was charged with 60 parts of propylene, 87.7 parts of a solution comprised of about 40% by weight tertiary butyl hydroperoxide in tertiary butyl alcohol and 2.3 parts of a catalyst solution obtained in Example IB above, and containing 11,000 ppm of molybdenum. The epoxidation reaction was effected at 121° and 500 psia over a period of time sufficient to obtain a tertiary butyl hydroperoxide conversion of 98%, based on the tetiary butyl hydroperoxide charged. The yield of desired propylene oxide product was 96.4%.

An epoxidation reaction as described in Example VI, above was carried out, except that the catalyst employed in the epoxidation reaction consisted of a catalyst solution containing 5500 ppm of molybdenum and was obtained as described above in Example IV. The yield of desired propylene oxide product was 95.7%.

Example VI demonstrate the obtainment of improved yields of desired propylene oxide product by use of catalyst compositions of the invention derived from oxalic acid, as compared with typical catalyst solutions obtained from molybdenum metal described in the prior art.

EXAMPLE VII

An epoxidation catalyst solution was prepared by blending, at room temperature, 50 parts of the catalyst described in Example IB, above and 29 parts of a liquid evaporation residue containing 1.9 weight percent molybdenum obtained by the wiped film evaporation, effected at 400° F. and 1 atmosphere pressure, of a heavy liquid fraction derived from the epoxidation of propylene with tertiary butyl hydroperoxide until 67% of the charge is removed overhead, as described in Example IV of U.S. Pat. No. 3,819,663.

An epoxidation reaction as described in Example VI, above, was carried out while employing the catalyst in concentration of 170 ppm molybdenum. A yield of desired propylene oxide product of 95.3 percent was obtained based on the tertiary butyl hydroperoxide charged.

I claim:

1. In the method for producing a molybdenum-containing catalyst useful as an organic soluble epoxidation catalyst comprising reacting molybdenum metal with a peroxy compound in the presence of at least one saturated monohydroxy alcohol, the improvement which comprises effecting said reaction in the presence of an organic dicarboxylic acid present in an amount of at least 0.2 parts, by weight, per part of molybdenum metal, thereby resulting in a stable molybdenum-containing catalyst solution.

2. The process of claim 1 wherein the final molybdenum-containing catalyst solution composition contains at least 0.5% molybdenum.

3. The process of claim 1 wherein the final molybdenum-containing catalyst solution contains at least 1%, by weight, molybdenum.

4. The process of claim 1 wherein said peroxy compound is a member selected from the group consisting of an organic hyrdroperoxide, an organic peracid and hydrogen peroxide.

5. The process of claim 4 wherein said peroxy compound is an organic hydroperoxide.

6. The process of claim 5 wherein the reaction is additionally carried out in the presence of a polyhydroxy alcohol present in an amount not greater than about 20% by weight, of the monohydroxy alcohol.

7. The process of claim 5 wherein said monohydroxy alcohol is methyl alcohol.

8. The process of claim 5 wherein said monohyrdoxy alcohol is tertiary butyl alcohol.

9. The process of claim 5 wherein said organic dicarboxylic acid contains of from about 2 to 18 carbon atoms.

10. The process of claim 9 wherein said organic dicarboxylic acid is oxalic acid.

11. The process of claim 9 wherein said organic dicarboxylic acid is malonic acid.

12. The process of claim 9 wherein said organic dicarboxylic acid is succinic acid.

13. The process of claim 9 wherein said organic dicarboxylic acid is phthalic acid.

14. The process of claim 10 wherein the proportion by weight of oxalic acid to molybdenum metal present ranges between about 0.2:1 to 4:1.

15. The process of claim 14 wherein the monohydroxy alcohol is tertiary butyl alcohol and the polyhyrdoxy alcohol is propylene glycol.

16. The process of claim 1 wherein said reaction is effected at a temperature in the range of from about 25° C. to 120° C.

17. The process of claim 16 wherein said reaction is effected at a temperature in the range of from about 50° C. to 100° C.

18. The molybdenum-containing catalyst produced in accordance with the method of claim 1.

19. The molybdenum-containing catalyst produced in accordance with the method of claim 10.

* * * * *